United States Patent [19]

Vermeiren

[11] Patent Number: 4,471,295
[45] Date of Patent: Sep. 11, 1984

[54] DEVICE FOR DETECTING THE VARIATION OF A CAPACITIVE IMPEDANCE HAVING DIELECTRIC CONSISTING OF A LUBRICANT

[75] Inventor: Karel N. Vermeiren, Woerden, Netherlands

[73] Assignee: SKF Industrial Trading Company B.V., Nieuwegein, Netherlands

[21] Appl. No.: 353,247

[22] Filed: Mar. 1, 1982

[30] Foreign Application Priority Data

Mar. 18, 1981 [NL] Netherlands .......................... 8101310

[51] Int. Cl.³ ............................................. G01R 27/26
[52] U.S. Cl. ..................................... 324/61 R; 73/10
[58] Field of Search ................ 73/9, 10; 324/61 R, 324/61 QS, 61 QL

[56] References Cited

U.S. PATENT DOCUMENTS

| | | | |
|---|---|---|---|
| 1,960,168 | 5/1934 | Schoenberg | 324/61 R |
| 2,177,528 | 10/1939 | Kidd | 324/61 R |
| 2,662,408 | 12/1953 | Ellison | 324/61 R |
| 2,742,609 | 4/1956 | Black | 324/61 R |
| 3,609,735 | 9/1971 | Dauterman. | |
| 3,901,216 | 8/1975 | Felger | 324/61 QL X |
| 3,990,960 | 11/1976 | Ellison. | |

FOREIGN PATENT DOCUMENTS

| | | | |
|---|---|---|---|
| 21524 | 1/1981 | European Pat. Off.. | |
| 2482254 | 11/1981 | France | 73/10 |

Primary Examiner—Stanley T. Krawczewicz
Assistant Examiner—Jose M. Solis
Attorney, Agent, or Firm—Daniel M. Rosen

[57] ABSTRACT

The invention relates to a device for measuring the variation of a capacitive impedance, the dielectric of which consists of a lubricant, provided with an oscillator that supplies a signal having a predetermined frequency to the capacitive impedance by way of a bias impedance.

The device according to the invention is characterized by a current measuring means delivering a signal depending on the current passing through the capacitive impedance to a converter the output of which delivers a direct current voltage signal coinciding with the instantaneous value of the capacitive impedance.

7 Claims, 1 Drawing Figure

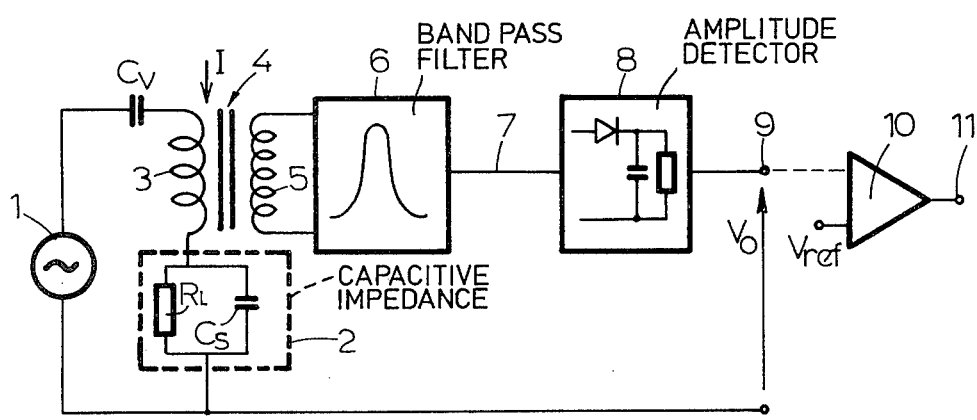

DEVICE FOR DETECTING THE VARIATION OF A CAPACITIVE IMPEDANCE HAVING DIELECTRIC CONSISTING OF A LUBRICANT

BACKGROUND OF THE INVENTION

1. Field of the Invention

The invention relates to a device for detecting the variation of a capacitive impedance, the dielectric of which consists of a lubricant, provided with an oscillator that supplies a signal having a predetermined frequency to the capacitive impedance by way of a bias impedance.

2. Description of the Prior Art

In a known device of this kind, output signals are delivered that provide a measure of the thickness of a lubricant film between surfaces rolling or sliding against each other and of the percentage contact during a definite interval of measurement. Although this known device has the advantage that especially accurate results of measurement are obtained, the known device is comparatively complicated, and costs of manufacture are high. In practice, however, a need is felt for a simple and inexpensive device whereby the lubrication of parts in motion relative to each other and lubricated with a lubricant can be evaluated, and in particular the quality of said lubricant, as, for example, in bearing systems where oil film monitoring is very important.

The present invention, then, intended to provide a device of the kind initially mentioned, satisfying this requirement.

SUMMARY OF THE INVENTION

For the purpose, the device according to the invention is characterized by a current measuring means delivering a signal depending on the current passing through the capacitive impedance to a converter the output of which delivers a direct current voltage signal corresponding to the instantaneous value of the capacitative inpedance.

In this way, a device of especially simple construction is obtained, that can be manufactured at comparatively low cost. Since the instantaneous value of the capacitive impedance depends on the relative dielectric constant and the leak resistance of the lubricant, the direct current voltage signal obtained is a measure of the quality of the lubricant and the lubrication of the parts lubricated with the lubricant. Furthermore, in the device according to the invention no contact need be made with moving parts, since exclusively the quality of the lubricant is to be measured between a sensor ring and static part.

According to an advantageous embodiment of the invention, the current measuring means consists of a current transformer the primary winding of which is contained in the connection between the bias impedance and the capacitive impedance, while the secondary winding is connected to the converter. Here, according to the invention, the converter may be provided with a band pass filter tuned to the predetermined frequency of the oscillator, the input of the filter being connected to the secondary winding of the current transformer while the output is connected to an amplitude detector emitting the direct current voltage signal.

The device according to the invention may therefore be assembled from inexpensive components, so that the cost is low, enabling the device to be employed in a variety of fields.

According to the invention, for examle, a comparator may be connected to the output of the converter, which comparator compares the direct current voltage signal with a reference value and emits an alram signal when that value is trangressed. Thus the device can, for example, monitor the quality of oil in the crankcase of an internal combustion engine or of oil in the transmission and the like, automatically sounding an alarm signal when the oil must soon be changed. For this purpose, the capacitive impedance according to the invention comprises two contact means in the form of metal strips or pins, in contact with the lubricant.

The device according to the invention may likewise be used to monitor the lubrication of wheel bearings of a vehicle, for which purpose the capacitive impedance comprises two contact means consisting respectively of an inner or outer race of a bearing and a metal strip formed on the seal of the bearing.

BRIEF DESCRIPTION OF THE DRAWING

The invention will now be described in more detail with reference to the drawing, in which an embodiment of the invention is represented by way of example.

The FIGURE shows a combination circuit/block diagram of the preferred embodiment of the present invention.

DESCRIPTION OF THE PREFERRED EMBODIMENT

In the figure, an oscillator 1 is connected by way of a bias impedance, consisting preferably of a capacitance $C_v$, to a capacitive impedance 2 whose dielectric consists of a lubricant and which itself consists of a capacitance $C_s$ and a leak resistance $R_L$. The oscillator 1 delivers a sinusoidal signal having a predetermined frequency $f_o$ of, for example, 0.5 MHz. Hence a current I will pass through the capacitive impedance 2, such that $$I = \frac{U}{\sqrt{R_L^2 + (1/C_s\omega)^2}}$$

where U is the voltage across the impedance 2. The capacitance of the condensor $C_s$ is here a function of the relative dielectric constant $\epsilon_r$ of the lubricant.

By measuring the current I, therefore, the variation of the impedance 2 can be determined. For this purpose, the primary winding 3 of a current transformer 4 is included in the connection between the capacitance $C_v$ and the impedance 2. The secondary winding 5 is connected to a band pass filter 6 tuned to the frequency of the oscillator 1, so that at the output 7 of the band pass filter 6, an amplitude-modulated signal of frequency $f_o$ appears. The band filter 6 may be a ceramic filter or may consist of a tuned circuit composed of the secondary winding 5 and a condensor in parallel therewith.

To the output 7 of the band pass filter 6, an amplitude detector 8 is connected, which may take the form of a peak detector as schematically indicated in the drawing. At the output 9 of the amplitude detector 8, a direct current voltage signal $V_o$ is available, corresponding to the instantaneous value of the capacitive impedance 2. If desired, an amplifier (not shown) may be connected to the output 8 as well, bringing the direct current voltage signal $V_o$ to a suitable level.

From the foregoing, it will be seen that the invention provides an especially simple device for detecting a predetermined of the capacitive impedance 2, which is composed of inexpensive parts, so that the of the device cost is low. The direct current voltage signal $V_o$ obtained depends on the relative dielectric constant $\epsilon_r$ and the leak resistance $R_L$, which factors in turn depend on the quality of the lubricant.

The device described may thus be employed in various fields to check the quality of a lubricant during service. The capacitive impedance 2 may, for example, comprise two contact means acting as "capacitor plates" and taking the form of metal strips or pins in contact with the lubricant. Such strips or pins may for this purpose be installed from each other in the crankcase of an internal combustion engine or in a gear box or the like, the direct current voltge signal $V_o$ serving to indicate when the quality of the oil has deteriorated to such an extent that the oil must be changed.

Here the output 9 of the amplitude detector may, for example, be connected to one input of a comparator 10, as indicated by a dotted line in the drawing. To the other input of the comparator 10, a reference voltage $V_{ref}$ is connected, the output 11 of the comparator 10 automatically giving an alarm signal if the reference voltage $V_{ref}$ is exceeded by the direct current voltage signal $V_o$. The output 11 may, for example, actuate a signal light indicating to the user that an oil change will be required shortly.

According to the invention, the contact means of the capacitive impedance may alternatively take the form respectively of an inner or outer race of a bearing and a metal strip formed on the seal of the bearing. In this way the lubrication of the bearing can be monitored.

Inasmuch as, in the device described, only the current I through the capacitive impedance need be measured, the important advantage is gained that in principle no contact with moving parts is required to detect the state of lubrication or the quality of the lubricant.

Of course the device according to the invention may alternatively be used to measure the thickness of a film of lubricant in a bearing. In that case, the contact means of the capacitive impedance 2 consist of the inner and the outer race of the bearing. The value of the capacitive impedance 2 detected will then also depend on the thickness of the lubricant film, since a decreasing thickness of the film implies a decreasing thickness of the dielectric. By employing the comparator 10 and, for example, a counter, counting the number of transgressions of the reference voltage $V_{ref}$ per interval of meausrement, the percentage contact time may be measured as well.

The invention is not limited to the embodiment described by way of example in the foregoing, which may be modified in various ways without departing from the spirit and scope of the invention.

I claim:

1. A device for directing the variation of a capacitive impedance, comprising:
   (a) a capacitive impedance in which a lubricant serves as the dielectric;
   (b) a bias impedance;
   (c) an oscillator operatively connected to said capacitive impedance by way of said bias impedance for outputting a signal of predetermined frequency to said capacitive impedance;
   (d) a current transfromer having a primary winding and a secondary winding, said bias impedance and said capacitive impedance being operatively coupled by way of said primary winding:
   (e) an amplitude detector; and
   (f) a band pass filter tuned to said predetermined frequency, the input of said filter being connected to said secondary winding of said current transformer and the output of said filter being connected to the input of said amplitude detector;
   wherein said current transformer delivers a signal to said filter in response to current flowing through said capacitive impedance, and in response to receipt of said filtered signal said amplitude detector outputs a direct current voltage signal corresponding to the instantaneous value of said capacitive impedance.

2. A device according to claim 1 wherein said band pass filter comprises a condenser connected in parallel with said secondary winding of said current transformer.

3. A device according to claim 1 further comprising a reference voltage supply for supplying a reference voltage signal and a comparator having first and second inputs, wherein the output of said amplitude detector is connected to said first input and said reference voltage supply is connected to said second input, such that said compartor compares said direct current voltage signal and said references voltage signal and outputs as alarm signal in response to agreement of said voltage signals.

4. A device according to any one of claims 1-3, wherein said capacitive impedance comprised first and second contact means arranged to contact said lubricant.

5. A device according to claim 4 wherein said contact means comprise metal strips.

6. A device according to claim 4 wherein said contact means comprise metal pins.

7. A device according to claim 4 wherein said first contact means comprises a race of a bearing and said second contact means comprises a metal strip formed on a seal of said bearing.

* * * * *

UNITED STATES PATENT AND TRADEMARK OFFICE
CERTIFICATE OF CORRECTION

PATENT NO. : 4,471,295
DATED : September 11, 1984
INVENTOR(S) : Karel N. Vermeiren It is certified that error appears in the above-identified patent and that said Letters Patent are hereby corrected as shown below:

Column 1, line 30, before "intended" insert -- is --.

Column 2, line 57, after "band" insert -- pass --.

Column 3, line 3, after "predetermined" insert -- variation --.

Column 3, line 15, after "installed" insert -- insulated --.

Column 4, line 4, delete "directing" and insert -- detecting --.

Column 4, line 39, delete "compartor" and insert -- comparator --.

Column 4, line 43 delete "comprised" and insert -- comprises --.

Signed and Sealed this

Eighth Day of October 1985

[SEAL]

Attest:

DONALD J. QUIGG

Attesting Officer

Commissioner of Patents and Trademarks—Designate